United States Patent [19]
Batlaw

[11] Patent Number: 6,069,276
[45] Date of Patent: May 30, 2000

[54] OXYALKYLENE-SUBSTITUTED M-AMIDOANILINE INTERMEDIATE

[75] Inventor: Rajnish Batlaw, Spartanburg, S.C.

[73] Assignee: Milliken & Company, Spartanburg, S.C.

[21] Appl. No.: 09/263,906

[22] Filed: Mar. 5, 1999

[51] Int. Cl.$^7$ ..................................... C07D 41/04
[52] U.S. Cl. ........................ 564/218; 534/729; 534/855
[58] Field of Search ............................ 564/218; 534/729, 534/855

[56] References Cited

U.S. PATENT DOCUMENTS

| | | | |
|---|---|---|---|
| 2,118,661 | 5/1938 | Baumann | 534/855 |
| 2,155,755 | 4/1939 | Felix et al. | 534/855 |
| 2,286,795 | 6/1942 | Dickey et al. | 534/855 |
| 2,436,100 | 2/1948 | Dickey | 534/855 |
| 2,771,466 | 11/1956 | Towne et al. | 534/795 |
| 4,113,721 | 9/1978 | Hauser et al. | 534/729 |
| 4,871,371 | 10/1989 | Harris | 534/729 X |

FOREIGN PATENT DOCUMENTS

| | | | |
|---|---|---|---|
| 1070185 | 3/1993 | China . | |
| 2811067 | 9/1978 | Germany | 534/855 |
| 45-034945 | 11/1970 | Japan . | |
| 53-130381 | 11/1978 | Japan | 534/855 |
| 57-040559 | 3/1982 | Japan . | |
| 59-187061 | 10/1984 | Japan . | |
| 59-204658 | 11/1984 | Japan . | |
| 60-044556 | 3/1985 | Japan . | |
| 159759 | 1/1993 | Poland . | |

*Primary Examiner*—Fiona T. Powers
*Attorney, Agent, or Firm*—Terry T. Moyer; William S. Parks

[57] ABSTRACT

This invention relates to very specific oxyalkylene-substituted m-amidoaniline compounds as intermediates for the production of poly(oxyalkylene)-substituted diazo (or other type) colorants. Such an inventive intermediate compound is produced in a single step by reacting an oxyalkylene oxide or alkoxy oxyalkylester having at least three carbon atoms (branched or unbranched), glycidol, or a glycidyl group directly with m-acetoamidoaniline (as a preferred example) at a relatively low temperature. Propylene oxide is the preferred compound. The propylene oxide selectively reacts with the amine group on the base compound without propoxylating the amido group. Such a specific method thus does not require extra time- and cost-consuming steps of protecting the amido nitrogen from attack. After production, this intermediate may be reacted with, for example, a diazotized aromatic amine to ultimately form a diazo colorant. The resultant oxypropylene groups may subsequently be reacted with other compounds, such as anhydrides, isocyanates, esters, and the like, to produce any number of different colorants.

2 Claims, No Drawings

OXYALKYLENE-SUBSTITUTED M-AMIDOANILINE INTERMEDIATE

FIELD OF THE INVENTION

This invention relates to very specific oxyalkylene-substituted m-amidoaniline compounds as intermediates for the production of poly(oxyalkylene)-substituted diazo (or other type) colorants. Such an inventive intermediate compound is produced in a single step by reacting an oxyalkylene oxide or alkoxy oxyalkylester having at least three carbon atoms (branched or unbranched), glycidol, or a glycidyl group directly with m-acetoamidoaniline (as a preferred example) at a relatively low temperature. Propylene oxide is the preferred compound. The propylene oxide selectively reacts with the amine group on the base compound without propoxylating the amido group. Such a specific method thus does not require extra time- and cost-consuming steps of protecting the amido nitrogen from attack. After production, this intermediate may be reacted with, for example, a diazotized aromatic amine to ultimately form a diazo colorant. The resultant oxypropylene groups may subsequently be reacted with other compounds, such as anhydrides, isocyanates, esters, and the like, to produce any number of different colorants.

DISCUSSION OF THE PRIOR ART

All U.S. and/or foreign patents cited within this specification are hereby incorporated by reference. N,N-dialkylamidoaniline couplers are used as couplers in reactions with diazonium salts made from substituted aromatic amines to make diazo (or other type) colorants. However, the preparation of potentially beneficial poly(oxyalkylenated) derivatives of such amidoanilines [and thus poly(oxyalkylenated) diazo colorants] has not been possible since oxyalkylenation proceeds on the amide nitrogen when greater than two moles of alkylene oxide are reacted with the amidoaniline base compound. It has been observed that the oxyalkylenation of the amide nitrogen in addition to the oxyalkylenation of the free amine results in a diazo colorant with varied absorption measurements pertaining to wavelength, strength, and sharpness when compared to the colorant produced from the coupler oxyalkylenated only on the free amine. This is attributable to the absence of the free hydrogen on the amide nitrogen which permits beneficial hydrogen bonding between pendant groups on the diazo colorant which, in turn, decreases variations in absorption measurements by stabilizing the colorant in substantially one alignment. Thus, the resultant colorant provides brighter colorations than does the diazo containing the poly(oxyalkylenated) amide. Furthermore, the presence of poly(oxyalkylene) groups only on the free amine also permits further modifications of the physical and chemical properties of the diazo through subsequent reaction of the free hydroxyl groups with electrophiles such as anhydrides, isocyanates, esters, benzochlorides, and the like. Thus, better coloring is provided where non-oxyalkylenated amide constituents are present on the diazo colorant; however, versatility of coloring is also available where poly(oxyalkylene) groups are present on the chromophore as well. Thus, there exists a need to develop a poly(oxyalkylenated) colorant which also possesses the all-important free amido group. Such a colorant is not easily made through reaction of an already-formed diazo colorant. The amide nitrogen remains highly susceptible to electrophilic attack by the oxyalkylene substituent and is very difficult to protect prior to such a reaction. Thus, it has been determined an intermediate providing the ability of producing such poly(oxyalkylene) constituents on an aromatic ring without attacking the amide nitrogen is required to produce such beneficial colorants.

The traditional reactions of ethylene oxide or propylene oxide with the amidoaniline compound in the presence of a basic catalyst and at elevated temperatures would result in oxyalkylene substitution on all the nitrogens present, including on the amido moiety. Thus, the formation of a poly(oxyalkylenated) amidoaniline intermediate has not previously been possible.

An oxyethylene (and not polyoxyethylene) has been developed through the addition of about 2 moles of ethylene oxide to acetylamino anisole in the presence of water. This compound is disclosed in Polish patent 159,759, to Jerczynski et al. and in Chinese patent 1,070,185, to Liu et al. Such a compound does not provide the benefits of a poly(oxyalkylenated) colorant since only two oxyethylene groups total are bonded to the amine group. Furthermore, due to the high reactivity of ethylene oxide in greater amounts, there would be no real possibility of producing a poly(oxyalkylene) compound without also oxyalkylenating the amide nitrogen, thus preventing the formation of the desired improved colorant as discussed above. Thus, this compound does not provide the desired benefits, at least not without attempting to protect the free amido hydrogen which is both time-consuming and cost-prohibitive. Thus, there exists a need to develop a proper diazo intermediate which enables the production of a bright, poly(oxyalkylenated) colorant. The prior art has not accorded such an improved intermediate to the colorant industry.

DESCRIPTION OF THE INVENTION

It is thus an object of the invention to provide a specific propoxylated m-amidoaniline intermediate for the production of an oxyalkylenated diazo colorant. It is another object of this invention to provide a method of forming a specific propoxylated m-amidoaniline intermediate which is a one-step process. Yet another object of this invention is to provide a relatively inexpensive method for producing such beneficial oxyalkylenated diazo (or other type) colorants, the physical and chemical properties of which can be easily modified through subsequent reaction of the free hydroxyl groups with electrophiles such as anhydrides, isocyanates, esters, benzochlorides, and the like.

The present invention encompasses a method of making a compound as defined by the Formula (I)

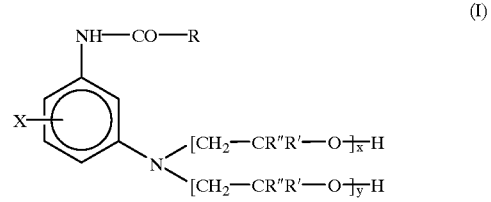

wherein R is selected from the group consisting of hydrogen, halo, formyl, $C_1$–$C_{20}$ alkoxy, and $C_1$–$C_{20}$ alkyl; wherein R' is selected from the group consisting of $C_1$–$C_{20}$ alkoxy, $C_1$–$C_{20}$ polyoxyalkoxy, $C_1$–$C_{20}$ alkylester, and $C_1$–$C_{20}$ alkyl; wherein R" is H or $CH_2R'$; and wherein x and y may be the same or different and are positive integers, wherein x+y is at least 1;

said method comprising the reaction of propylene oxide with a m-amidoaniline compound of the Formula (II)

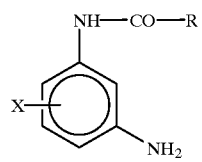

wherein R is $C_1$–$C_{20}$ alkyl, and X is selected from the group consisting of hydrogen, halo, nitroso, nitro, cyano, $C_1$–$C_{20}$ alkoxy, and $C_1$–$C_{20}$ alkyl. Preferably R is methyl, R' is methyl, X is methoxy, and x and y are independently either 1 or 2. The invention also covers the actual compound of Formula (I), above, as well as colorants made therefrom.

It has surprisingly been found that the aforementioned method produces the desired poly(oxyalkylenated) amidoaniline compound without resulting in the formation of oxyalkylene groups at the site of the free amido hydrogen. As noted above, previous reactions have attached only single oxyethylene groups to amino pendant groups on amido anilines without the use of base catalysts, but with the utilization of water as a catalyst. These prior reactions result in the formation of merely 2 moles total of oxyethylene on the target compound. The addition of any more ethylene oxide would most likely result in the oxyalkylenation of the free amido hydrogen, as noted above, which would thus render the compound useless for forming the desired colorants.

In the preferred inventive method, direct reaction with the less reactive propylene oxide is preferably utilized to effectuate the desired reaction without simultaneously driving the attack of oxypropylene groups to the free amido hydrogen. This is accomplished even with excess amounts of propylene oxide added (up to 15 moles and higher) and at a relatively low reaction temperature (from about 120 to about 250° F.). Thus, this controlled reaction permits greater selectivity of the site of propylene oxide attack by "slowing" the overall reaction. In turn, then, the ability to perform such a procedure in a one-step process translates into lower costs for the manufacturer of the ultimately produced colorant (i.e., diazo-, disazo-, triphenylmethane-derivative colorants, and the like) as well as for the end-user of products colored with such compounds.

In order for this reaction to be successful, any reactive compound including any alkylene oxide or alkoxy alkylester having at least three carbon atoms (branched or unbranched), glycidol, or glycidyl group may be utilized (again, propylene oxide is preferred) and is added with no base present. Surprisingly, it has been found through this inventive reaction, any number of moles of such reactive compound can be added to the amidoaniline without reacting with the free amido nitrogen. Thus, a polymeric colorant intermediate [i.e., a poly(oxypropylenated) colorant intermediate] may be formed through this inventive procedure. Theoretically, any number of moles of the preferred propylene oxide reactive group may be utilized in this reaction, with at most 15 preferred, at most 10 more preferred, and at most 4 most preferred. The reaction temperature may range from about 120 to about 250° F., with 135 to about 220° F. preferred, 145 to about 200° F. more preferred and 155 to about 200° F. most preferred. The reaction may be conducted in a suitable solvent such as acetic acid or water. A certain degree of propoxylenation will theoretically occur at the free amido hydrogen site; however, such a degree is severely limited in this inventive procedure and any such product can be separated from the desired oxypropylenated amidoaniline intermediate. Thus, up to about 15% of the overall product may comprise the unwanted aniline compound comprising the oxypropylenated groups in the free amido hydrogen location; preferably, this level is lower than 10%, more preferably, below 5%, and most preferably, naturally, this amount would be 0%.

This inventive reaction appears to work with any amido aniline conforming with Formula (II)

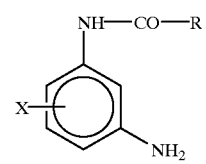

wherein R is $C_1$–$C_{20}$ alkyl and X is selected from the group consisting of hydrogen, halo, nitroso, nitro, cyano, $C_1$–$C_{20}$ alkoxy, and $C_1$–$C_{20}$ alkyl. Preferably R is methyl and X is methoxy. The resultant intermediate compound is thus produced through the introduction of propylene oxide to the amidoaniline compound under controlled temperature and moisture conditions. This resultant intermediate is represented by Formula (I):

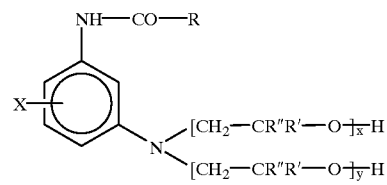

wherein R is selected from the group consisting of hydrogen, halo, formyl, $C_1$–$C_{20}$ alkoxy, and $C_1$–$C_{20}$ alkyl; wherein R' is selected from the group consisting of $C_1$–$C_{20}$ alkoxy, $C_1$–$C_{20}$ polyoxyalkoxy, $C_1$–$C_{20}$ alkylester, and $C_1$–$C_{20}$ alkyl; wherein R" is H or $CH_2R'$; and wherein x and y may be the same or different and are positive integers, wherein x+y is at least 1. Again, preferably R is methyl, X is methoxy, x and y are independently either 1 or 2, R' is methyl, and R" is H.

This inventive intermediate can then be utilized in other reactions to form polymeric colorants. For instance, the reaction of the inventive intermediate with another aromatic amine produces a diazo. The inventive diazo can then be reacted with another aromatic amine to theoretically produce a disazo colorant.

DESCRIPTION OF THE PREFERRED EMBODIMENT

The preferred embodiments of this invention are provided below:

Intermediate Formation

The general method of making the preferred inventive intermediate is as follows:

EXAMPLE 1

250 parts of acetic acid were charged into a reactor vessel with 100 parts of 3-amino-4-methoxyacetanilide. To this, 165 parts of propylene oxide (an excess amount in a 5:2 molar ratio as compared with the acetanilide) were then added slowly while maintaining a temperature of about 150–175° F. and at a pressure from about 20 to about 60 psi. The reaction continued for about 2 hours at which time the product was derivatized by acetylating with an excess amount of acetic anhydride. The recovered product was then analyzed by electron spray mass spectroscopy, GC-MS and $^1$H NMR to be a compound corresponding generally with Formula (III):

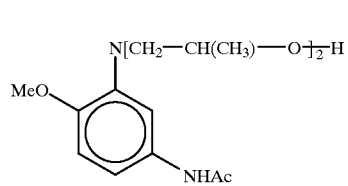
(III)

Very small proportions of the oxyalkylene substitution on the amido group may have taken place; however, such was not evident upon analysis through standard techniques.

Colorant Formation

The general method of making the preferred inventive colorant is as follows:

EXAMPLE 2

18 parts of NaNO$_2$ and 125 mL of concentrated sulfuric acid were charged to a reactor vessel followed by the addition of 16 parts of propionic acid and 84 parts of acetic acid, all while the temperature was kept at about 20° C. This solution was then allowed to cool to between about 0 and 5° C. Separately, 66 parts of 2-bromo-4,6-dinitroaniline were dissolved in 200 parts of concentrated sulfuric acid and added slowly to the solution above, again keeping the same low temperature of between about 0 and 5° C. The reactants were then stirred for about 1.5 hours. Simultaneously, a coupler was prepared by charging 62 parts of acetic acid, 12 parts of propionic acid, and 51 parts of the amido aniline of EXAMPLE 1 (N,N-polypropyleneoxy-3'-amino-4'-methoxyacetanilide in a separate reactor vessel kept at a temperature of about 20° C. After the 1.5 hours stirring time was completed, the two separate solutions were then admixed together at a temperature of about 15° C. The resultant mixture was stirred for another hour and subsequently neutralized and purified to obtain a brilliant blue diazo colorant of the Formula (IV):

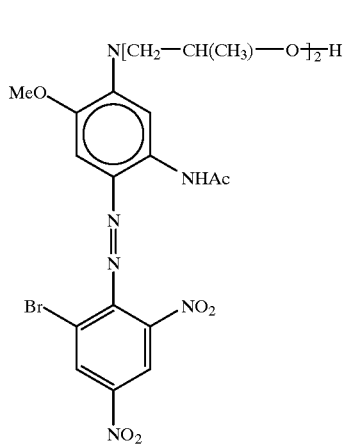
(IV)

There are, of course, many alternative embodiments and modifications of the present invention which are intended to be included within the spirit and scope of the following claims.

What I claim is:

1. A method of making a compound as defined by the Formula (I)

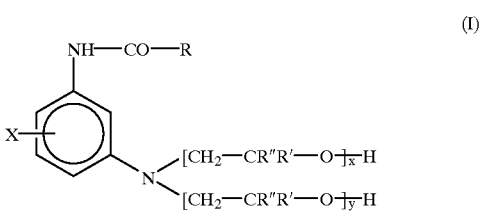
(I)

wherein R is selected from the group consisting of hydrogen, halo, formyl, $C_1$–$C_{20}$ alkoxy, and $C_1$–$C_{20}$ alkyl; wherein R' is selected from the group consisting of $C_1$–$C_{20}$ alkoxy, $C_1$–$C_{20}$ polyoxyalkoxy, $C_1$–$C_{20}$ alkylester, and $C_1$–$C_{20}$ alkyl; wherein R" is H or CH$_2$R'; wherein X is selected from the group consisting of hydrogen, halo, nitroso, nitro, cyano, $C_1$–$C_{20}$ alkoxy, and $C_1$–$C_{20}$ alkyl; and wherein x and y may be the same or different and are positive integers, wherein x+y is at least 2;

said method comprising the reaction of a reactive compound selected from the group consisting of C3–C22 branched or unbranched alkylene oxides, C3–C22 branched or unbranched alkoxy alkylesters, glycidol, and glycidyl, with an amidoaniline compound of the Formula (II)

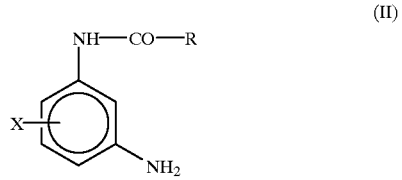
(II)

wherein R is $C_1$–$C_{20}$ alkyl and X is selected from the group consisting of hydrogen, halo, nitroso, nitro, cyano, $C_1$–$C_{20}$ alkoxy, and $C_1$–$C_{20}$ alkyl.

2. The method of claim 1 wherein R is methyl R' is methyl, X is methoxy, R" is H, x is 1 or 2, and y is 1 or 2.

* * * * *